United States Patent [19]

Lang et al.

[11] 4,061,647

[45] Dec. 6, 1977

[54] THIAZOLIDINE DERIVATIVES

[75] Inventors: Hans-Jochen Lang, Altenhain, Taunus; Roman Muschaweck, Frankfurt am Main, both of Germany

[73] Assignee: Hoechst Aktiengesellschaft, Frankfurt am Main, Germany

[21] Appl. No.: 709,075

[22] Filed: July 27, 1976

[30] Foreign Application Priority Data

July 29, 1975 Germany .............................. 2533821

[51] Int. Cl.² ........................................... C07D 277/18
[52] U.S. Cl. .......................... 260/306.7 T; 260/543 R; 260/556 C; 424/270
[58] Field of Search .................... 260/306.7 T, 556 C; 424/270, 232

[56] References Cited

U.S. PATENT DOCUMENTS

| 3,806,515 | 4/1974 | Houlihan et al. | ............. 260/306.7 T |
| 3,868,382 | 2/1975 | Giraudon | ...................... 260/306.7 T |

*Primary Examiner*—Richard J. Gallagher
*Attorney, Agent, or Firm*—Curtis, Morris & Safford

[57] ABSTRACT

The invention relates to thiazolidine derivatives having in 4-position a hydroxy group and a 3'-sulphamyl-phenyl substituent the phenyl ring of which is di-substituted by halogen or methyl, in 2 position an imino group and in 1-position an aliphatic or cycloaliphatic substituent. Said thiazolidines have diuretic activity.

The invention also relates to a process for the manufacture of said compounds.

7 Claims, No Drawings

THIAZOLIDINE DERIVATIVES

The present invention relates to thiazolidine derivatives of the general formula I

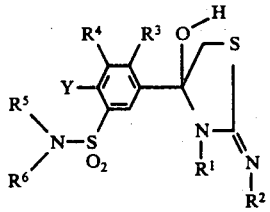

(I)

in which $R^1$ represents alkyl or alkenyl radicals of 1 to 4 carbon atoms, cycloalkyl groups of 3 to 6 carbon atoms, $R^2$ represents an alkyl or alkenyl group of 1 to 6 carbon atoms which may be substituted by alkoxy groups of 1 to 2 carbon atoms, cycloalkyl groups of 3 to 8 carbon atoms, phenylalkyl groups of 1 to 2 carbon atoms in the alkyl moiety, and in which $R^1$ and $R^2$ together may represent an alkylene chain of 2 to 4 carbon atoms which may be branched, Y represents chlorine, bromine or methyl and $R^3$ and $R^4$ represent hydrogen, chlorine, bromine or methyl, the two radicals $R^3$ and $R^4$ representing at the same time neither hydrogen, nor chlorine, bromine or methyl, $R^5$ and $R^6$ represent hydrogen or lower alkyl of 1 to 4 carbon atoms, $R^6$ may additionally represent a phenylalkyl group, and to their acid addition salts physiologically tolerated acids.

The invention furthermore relates to a process for preparing the compounds of the above general formula I, which comprises a. reacting compounds of the general formula II

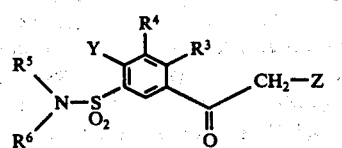

(II)

in which $R^3$, $R^4$, $R^5$, $R^6$ and Y have the meanings given above, and Z represents the radical of an activated ester of a mineral or organic acid, with thio-ureas of the general formula III, which may be present in the form represented by the two formulae IIIa and IIIb

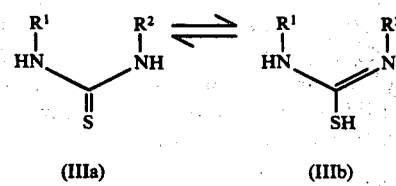

(IIIa)         (IIIb)

in which $R^1$ and $R^2$ have the meanings given above, or b. treating compounds of the general formula IV

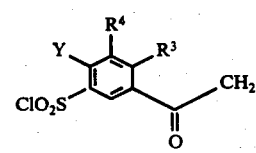

(IV)

in which $R^3$, $R^4$ and Y have the meanings given above, with a halogenating agent and reacting the α-halogenoketones so obtained of the general formula V

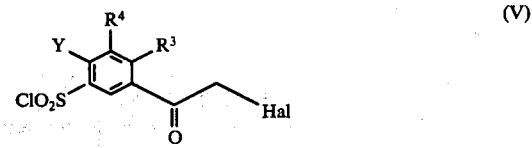

(V)

in which $R^3$, $R^4$ and Y have the meanings given above and Hal represents Cl or Br, if desired or required without isolation or purification, with thio-ureas of the formula III and reacting the thiazolidine derivatives obtained of the general formula VI

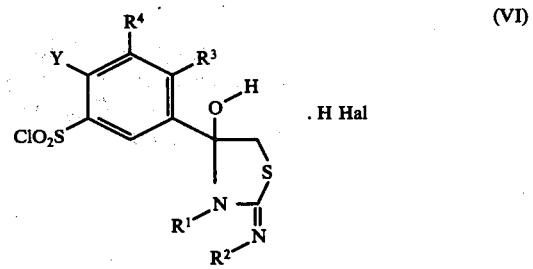

(VI)

in which $R^1$, $R^2$, $R^3$, $R^4$ and Y have the meanings given above, with ammonia, a primary or secondary amine of the general formula VII

(VII)

in which $R^5$ and $R^6$ have the meanings given above, or c. reacting compounds of the general formula VIII

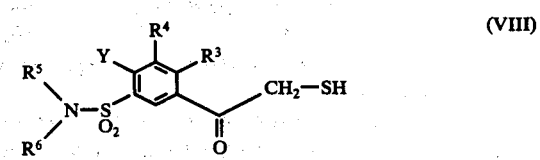

(VIII)

with compounds of the formula IX

(IX)

in which formulae $R^1$ through $R^6$ and Y have the meanings given above, and Hal represents chlorine or bromine, or d. reacting compounds of the formula VIII with carbodiimides of the formula X

$$R^1 - N = C = N - R^2$$ (X)

in which $R^1$ and $R^2$ have the meanings given above, or e. treating compounds of the general formula XI

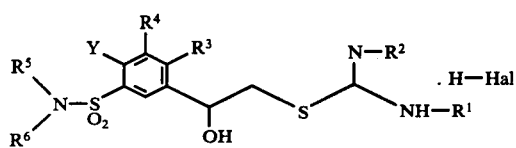

in which $R^1$ through $R^6$ and Y have the meanings given above and Hal represents chlorine or bromine, with an oxidizing agent, or f. reacting compounds of the general formula XII

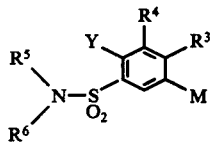

in which $R^5$ and $R^6$ are not hydrogen and Y, $R^3$ and $R^4$ are not bromine, but otherwise have the meanings given above, and M represents lithium or a MgBr group, with compounds of the general formula XIII

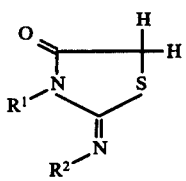

in which $R^1$ and $R^2$ have the meanings given above, and subjecting the reaction product obtained to hydrolysis, and, if desired, transforming the compounds of the general formula I obtained according to methods (a) to (f) with organic or mineral acids into their acid addition salts or the salts obtained of the compounds of the general formula I with bases into the free basic compounds of the formula I.

Mineral acids which may be used are, for example, hydrohalic acids such as hydrochloric acid and hydrobromic acid, as well as sulfuric acid, phosphoric acid and amido-sulfonic acid.

Organic acids which may be used are, for example, formic acid, acetic acid, benzoic acid, succinic acid, fumaric acid, maleic acid, lactic acid, tartaric acid, citric acid, salicylic acid, oxyethanesulfonic acid, ethylenediaminetetraacetic acid, methane-sulfonic acid, p-toluenesulfonic acid, etc.

The compounds of the formulae I and VI may also be present in their tautomeric forms:

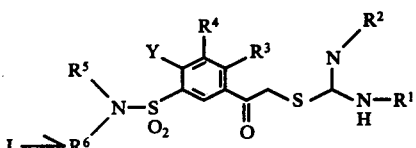

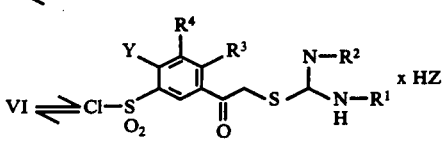

The compounds of the formula I of the invention may, in addition, also be present in their possible geometrical isomeric structures.

Over the open-chain tautomeric form I a, the cyclic compounds of the formula I, with different $R^1$ and $R^2$, are in equilibrium with the position-isomeric compounds of the formula I c and their acid addition salts

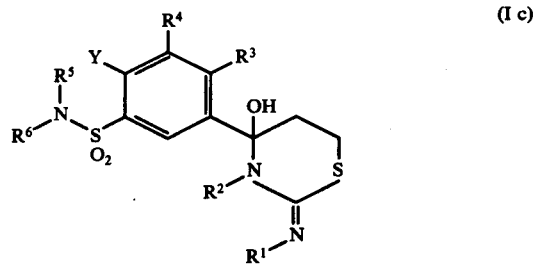

Which of the two cyclic isomers I or I c or their acid addition salts are present to a preponderant degree depends essentially on the different spatial filling of the substituents $R^1$ or $R^2$ in that the spatially smaller substituent fixes preferably in the position 3 of the thiazolidine ring system. For the sake of simplicity, only one of the possible isomeric or tautomeric forms of a substance is indicated for the compounds of the invention.

Method (a) is carried out advantageously by reacting the compounds of the formula II with the thio-ureas of the formula III in a molar ratio of 1 : 1 to 1 : 1.5. Higher molar excess amounts of thio-ourea generally do not give significant advantages. The reaction is advantageously carried out in an inert solvent, for example in polar organic solvents such as dimethylformamide, dimethylacetamide, dioxane, tetrahydrofurane, acetonitrile, nitromethane, diethylene-glycol-dimethyl ether, etc. As particularly advantageous reaction mediums proved acetic acid lower alkyl esters such as methyl acetate and ethyl acetate, lower alkohols containing 1 to 4 carbon atoms, in particular methanol, ethanol, isopropanol, and lower dialkyl ketones, for example acetone and methyl-ethyl ketone. Mixtures of the mentioned solvents may also be used as well as mixtures of the mentioned solvents with less appropriate solvents, for example methanol/benzene, ethanol/toluene, methanol/diethyl ether, ethanol/carbon tetrachloride, acetone/chloroform, it being of advantage that the solvent with a higher polarity be present in an excess amount. The reaction partners may be present in the respective solvent in suspended or dissolved form. Principally, the reaction partners may also be reacted without using a solvent, in particular in those cases where the respective thio-urea has a very low melting point, but in these cases side-reactions may occur by reason of the exothermic reaction course so that this process variant does not bring any advantages over the method of operation in solvents. The reaction proceeds moderately exothermically and can be carried out at between 0° and 100° C, preferably at between 10° and 70° C. Particularly advantageous proved a temperature range of from 20° to 55° C.

The reaction time depends largely on the reaction temperature and is between 2 minutes in the higher temperature ranges and 60 hours at lower temperatures. In the favourable temperature range, the reaction time is generally between 5 minutes and 40 hours.

In many cases the compounds I in the form of their acid addition salts separate during the reaction in a sparingly soluble form, in which case the yield may be increased optionally by subsequent addition of a suitable precipitant. As precipitants, there may be used, for example hydrocarbons such as benzene, toluene, cyclohexane, petroleum ether, ligroine, carbon tetrachloride; especially appropriate proved acetic acid lower alkyl esters containing 1 to 4 carbon atoms in the alkyl moiety, such as ethyl acetate and n-butyl-acetate, dialkyl ether containing 4 to 8 carbon atoms, such as diethyl ether, diisopropyl ether and di-n-butyl ether. If, after termination of the reaction, a solution is obtained, the salts of the compounds of the formula I are precipitated with one of the afore-mentioned precipitants, optionally after previous concentration of the reaction solution, or, advantageously, in order to remove inhomogeneous impurities, the solution is filtered into one of the mentioned precipitants, while stirring. Since the reaction of the compounds II with the thio-ureas III, if effected under optimum conditions, practically proceeds quantitatively, the crude products so obtained of the desired compounds are in most cases already analytically pure.

The thio-ureas III used are in most cases substances which are described in literature. They are obtained in known manner by the reaction of amines with isothiocyanates, carbon disulfide or thiophosgene (cf. Houben-Weyl, "Methoden der organischen Chemie", Vol. 9, page 884, 4th Edition, Georg-Thieme Verlag Stuttgart, 1955).

In the compounds of the formula II, there may be used as the radical of an activated ester Z, for example Cl, Br, I, —O—CO—$C_6H_4$—$NO_2$, $CH_3$—$SO_2$—O—, $C_2H_5$—$SO_2$—O—, $C_6H_5$—$SO_2$—O— and $CH_3C_6H_4$—$SO_2$—O—. They can be obtained by several methods.

In this way, the diazo-ketones of the general formula XIV

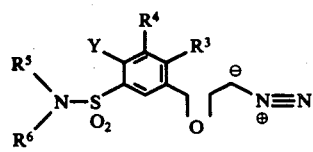

(XIV)

may be converted with acids into the ketones of the formula II.

Since diazoalkanes are extremely poisonous, explosive and difficult to manipulate, the compounds of the formula II in which $R^3$, $R^4$, $R^5$, $R^6$ and Y have the meanings given above and Z represents chlorine or bromine, are prepared in a more advantageous manner by reacting compounds of the general formula XV

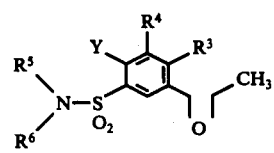

(XV)

with a suitable halogenating agent, for example with elementary chlorine or bromine, sulfuryl chloride, mono-chloro-urea, copper-II bromide, bromodioxane, N-bromosuccinimide under the conditions known from literature.

Finally, the compounds of the formula II may also be obtained by reacting under conditions known from literature the α-hydroxy-ketones of the general formula XVI

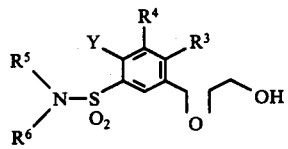

(XVI)

with the activated derivatives of organic and mineral acids such as methane-sulfonic acid chloride, ethane-sulfonic acid chloride, benzene-sulfonic acid chloride, p-toluene-sulfonic acid chloride, thionyl chloride, phosphorus trichloride, phosphorus tribromide, phosphorus oxide chloride, p-nitrobenzyl chloride, According to the method (b), sulfo-chlorides of the general formula IV are reacted with a halogenating agent, for example elementary chlorine, sulfuryl chloride, mono-chloro-urea, bromodioxane, N-bromo-succinimide, but in particular with elementary bromine or with copper-II bromide. In the halogenation of IV with bromine, the bromine is added dropwise, in diluted or undiluted form, to a solution or suspension of the equimolar quantity of IV in an inert solvent, for example a halogenated hydrocarbon such as chloroform or methylene chloride, in glacial acetic acid, preferably however in an acetic acid lower alkyl ester such as methyl acetate, ethyl acetate, n-butyl acetate or in a mixture of the mentioned solvents at temperatures in the range of from 0° to 50° C, preferably 10° to 35° C. Since ketone halogenations are catalyzed by acids, the reaction is initiated at the beginning by addition of catalytical amounts of an acid, suitably hydrobromic acid, or the protons required for the reaction are produced by the dropwise addition of a small amount of bromine and following heating of the reaction mixture until discoloration of the halogen, during which process the temperature range may also be surpassed for a short period of time. As diluents for the bromine to be added dropwise, there are suitable the above-mentioned inert solvents or mixtures thereof.

For brominating the compounds IV with copper-II bromide, the reaction is carried out in a manner analogous to that described in J.Org. Chem. 29, 3459 (1964), according to which the ketones IV are boiled with 2 moles of pulverized copper-II bromide in ethyl acetate or mixtures of ethyl acetate and chloroform which are free from water and alkohol until the dark colour of the copper-II bromide has vanished and a colourless precipitate of copper-I bromide has separated which can be isolated subsequently by filtration.

As chlorinating agent, there is suitable in particular sulfuryl chloride which is reacted with a solution or suspension of the compounds IV in a suitable solvent, preferably in a halogenated hydrocarbon, for example in chloroform or carbon tetrachloride. The reaction is carried out within a period of time of 5 to 30 hours, in a temperature range of from 10° to 100° C, preferably from 20° to 80° C, the reaction mixture is hydrolyzed with ice water, optionally after previous concentration, and the organic phases are worked up.

The solution or suspension obtained after the respective method of operation is suitably evaporated under reduced pressure and the compounds V obtained as residue are purified by crystallization in inert solvents, for example benzene, toluene, carbon tetrachloride, cyclohexane, petroleum ether, etc. It is more advantageous to react the compounds V so obtained without further purification in a suitable inert solvent with the equimolar amount of thio-urea III to the compounds of the general formula VI. If the halogeno-ketone V is reacted without previous isolation with the thio-ureas III, the quantity of the thio-urea III to be used is calculated on the respective ketone IV. The use of 1.5 moles of thio-urea may result in higher yields of VI, whereas higher excess amounts of III do not bring any significant advantages. As inert solvents, there may be used, for example pure dimethylformamide and dimethylacetamide, dioxane, tetrahydrofurane, acetonitrile, nitromethane, diethyleneglycol-dimethyl ether, etc. Particularly suitable solvents acetic acid lower alkyl esters, for example methyl acetate, ethyl acetate and n-butylacetate, as well as lower dialkyl ketones such as acetone and methyl-ethyl ketone. Mixtures of the above-mentioned solvents may also be used. The reaction proceeds moderately exothermically and is carried out at a temperature in the range of from 0° to 60° C, preferably from 20° to 40° C. The reaction times depend in particular on the reaction temperature used and are between 5 minutes and 40 hours.

The thiazolidines of the formula VI separate during the reaction in a sparingly soluble form and at the end of the reaction, optionally after previous concentration, the yield of VI can be increased by the addition of a suitable precipitant. As precipitants, the solvents used in method a) for the same purpose are suitable. If, after termination of the reaction, a solution is obtained, the compounds of the formula VI are precipitated, optionally after previous concentration of the reaction mixture with one of the above-mentioned precipitants or the reaction mixture is advantageously filtered into the respective solvent, while stirring. The compounds of the formula VI so prepared are in general distinguished by a high degree of purity. In any case, should a purification of the compounds VI be necessary, they can be recrystallized from a suitable inert solvent which is free from water and alcohol as far as possible, for example acetone, methyl-ethyl ketone, acetonitrile, nitromethane. The method of dissolution and reprecipitation is particularly advantageous, since it avoids strong thermic load of the compounds VI. For this purpose the respective raw product of the formula VI is dissolved in a pure and inert solvent, for example dimethylformamide, dimethyl-acetamide, acetone, acetonitrile, nitromethane, at a temperature in the range of from 0° to 30° C, the solution is optionally treated with charcoal and after filtration the compounds are precipitated with one of the above-mentioned precipitants.

The clearness of the reaction course in the reaction of the halogeno-ketones V with the thio-ureas III to the thiazolidines VI is insofar surprising as, on the other hand, the thio-ureas III react specifically with the bromo-ketone radical in V, without attacking the chloro-sulfonyl group, and, on the other hand, that the sulfochloride function in the compounds V and VI does not react with the hydroxy function of the compounds VI despite the presence of the thio-ureas III which reach as weak bases.

The sulfonic acid chlorides of the general formula VI so obtained are then reacted with ammonia or with an amine of the formula VII to the compounds of the formula I. Aqueous solutions of ammonia and of the amines VII as well as liquid ammonia or pure amines may be used in excess amounts, the excess ammonia or amine serving at the same time as solvent. The reaction may also be carried out in organic solvents, for example dimethylformamide, dimethylacetamide, dimethyl-sulfoxide, dioxane, tetrahydrofurane, diethyleneglycol-dimethyl ether, the lower alcohols of 1 to 4 carbon atoms, for example methanol, ethanol or isopropanol, being especially suitable. For the reaction of the sulfochlorides VI to the sulfonamides I, 1 mole of ammonia or amine VII in the presence of 2 moles of an auxiliary base are theoretically necessary. Accordingly, the reaction can be carried out in such a manner that at least 3 moles of ammonia or amine VII are used per mole of sulfochloride VI. In this reaction, the use of 3 to 7 moles of ammonia or amine VII per one mole of sulfochloride is advantageous, but greater excess amounts of VII may also be used. It is also possible to operate with 1 or 2 moles of ammonia or amine VII, if the operation is carried out in the presence of an auxiliary base, using about 1 to 6 molar equivalents of auxiliary base. As auxiliary bases, mineral and organic hydroxides, carbonates and bi-carbonates, as well as salt solutions of weak mineral or organic acids, the tertiary amines such as triethylamine, tri-n-butylamine, methyl-dicyclohexylamine, ethyl-dicyclohexylamine being particularly advantageous in all cases. The tertiary amine may likewise serve, if used in an excess amount, as reaction medium without addition of another solvent. The reaction proceeds exothermically and it is of advantage to cool and to work at temperatures in the range of from −35° to +60° C, preferably from +10° to +35° C. The reaction time should be at least 30 minutes and the reaction can be discontinued after 2 days at the latest, since longer reaction times do not bring essential advantages. A reaction time of 6 to 20 hours is preferred. Working up is advantageously carried out, optionally after removal by distillation of the amine and concentration, by diluting the reaction mixture with water whereupon the compounds I precipitate in a sparingly soluble form. If $R^5$ or $R^6$ in the compound I so prepared represents a hydrogen atom, the pH-value should be adjusted as far as possible to 7.5 to 8.5. Directly after the precipitation with water, the compounds I separate in the form of viscous oils which crystallize more or less rapidly in particular with small substituents $R^1$ and $R^2$. The crystallization can be accelerated by several treatments with a suitable solvent, for example water, ether, diisopropyl ether, carbon tetrachloride, petroleum ether, n-butylacetate, etc.

After the precipitation with water, the compounds I can also be extracted with a suitable solvent, preferably an acetic acid lower alkyl ester such as methyl acetate or ethyl acetate. After drying of the extract over a suitable drying agent, for example sodium or magnesium sulfate, the compounds I are obtained preferably by evaporation of the solution under reduced pressure.

The compounds I may also be converted into the corresponding acid addition salts without further isolation and purification by treatment with a protonic acid H—Z.

According to method (c), the compounds of the formula VIII are reacted in a solvent with the known compounds of the formula IX. As solvents, lower alcohols containing 1 to 4 carbon atoms as well as lower alkyl esters of acetic acid containing 1 to 4 carbon atoms in the alkyl moiety, for example methyl acetate and ethyl acetate, are particularly suitable. The reactions are carried out in general in a temperature range of from 0° to 60° C, preferably from 15° to 35° C, the reaction time being between 5 and 60 hours. Particularly suitable for this reaction are especially the compounds VIII which have at the sulfamoyl group, besides $R^5$ = hydrogen, a voluminous organic radical $R^6$, for example tert. butyl, or such compounds VIII in which $R^5$ and $R^6$ each have an organic radical as substituent.

For carrying out the method (d), the mercapto-ketones of the formula VIII are reacted in an anhydrous polar inert solvent, for example in dioxane, tetrahydrofurane, methyl acetate or ethyl acetate, with the carbodiimides of the formula X in a molar ratio of 1:1. Corresponding to that said for method (c), the substitution of $R^5$ and $R^6$ is preferred in the same way for the compounds of the formula VIII. The reactions can be carried out in a temperature range of from 0° to 40° C, preferably from 10° to 30° C, the reaction time being between 1 and 20 hours.

The compounds of the formula VIII used in the methods (c) and (d) may be prepared in various ways. For example, the compounds of the formula II can be converted with thiocarboxylic acids of the formula XVII

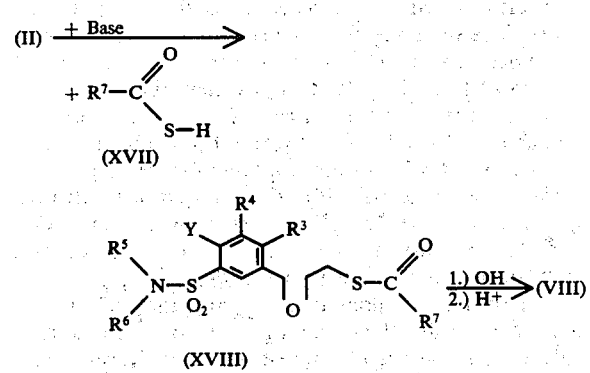

preferably with thio-acetic acid ($R^7$ = $CH_3$) in the presence of one equivalent of base, for example KOH, in an aqueous or alcoholic medium into the thio-esters of the general formula XVIII which are hydrolyzed in a weakly alkaline medium to the compounds of the formula VIII.

Another possibility consists in the reaction of the compounds of the formula II with alkali metal hydrogeno-sulfides in an inert solvent such as sodium or potassium bisulfide in dimethylformamide at temperatures between 0° and 40° C. The methods yielding the compounds VIII are known from literature.

According to method (c), the compounds of the general formula XI are converted with the aid of a suitable oxidizing agent, preferably with active manganese-IV oxide, into the compounds of the formula I or their acid addition salts. As solvents, preferably halogenated hydrocarbons such as methylene chloride, chloroform, tetrachloroethane are used and the reaction is carried out at temperatures in the range of from 0° to 40° C, preferably from 20° to 30° C, over a period of time of 10 to 60 hours.

The compounds of the formula XI are obtained by converting the halogenoketones of the formula II, in which Z preferably represents chlorine or bromine, for example according to the method described in Arzneimittelforschung 22, 2095 (1972) with a suitable reducing agent, preferably with sodium boronhydride in methanol at temperatures between 0° and 25° C into compounds of the formula XIX

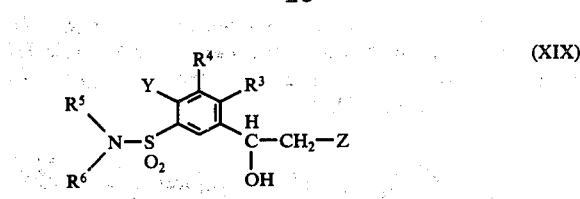

As alkyl-halides, the compounds of the formula XIX react with the thio-ureas of the formula III to the iso-thio-uronium salts of the formula XI. The reaction conditions correspond to those indicated for method (a).

According to method (f), compounds of the formula XII in which $R^5$ and $R^6$ are different from hydrogen and $R^3$ and $R^4$ are different from bromine are reacted with the compounds of the formula XIII which are known from literature. The compounds XII and XIII are advantageously reacted in a molar ratio of 1:1 to 1:1.5 in an inert and anhydrous solvent usually employed for metal-organic reactions, preferably ether or tetrahydrofurane. For this purpose a temperature range of from 0° to 60° C is chosen, the reaction being preferably carried out at temperatures between 15° and 35° C and the reaction time being between 1 and 30 hours. The reaction is carried out by dropwise adding a solution of the compounds XIII to a solution of the compounds XII, but the inverse method of operation is particularly advantageous in which the solution of 1 mole of the metal-organic compound XII is added dropwise to a solution of 1 to 1.5 mole of the compounds XIII in one of the above-indicated solvents. After completion of the reaction, the reaction products are hydrolyzed in a manner usual for metal-organic reactions, for example by introducing the reaction mixture at temperatures in the range of from −5° to +20° C, while maintaining a pH-range of from 6 to 8, into an aqueous saturated solution of ammonium chloride. Further working up of the compounds of the formula I so obtained is effected in a manner analogous to that described under method (b). The compounds of the formula XII used in method (f) are prepared, for example by brominating in the m-position to the nitro group compounds of the formula XX

reducing the $NO_2$ group and converting the amino compound so obtained by diazotization, Meerwein reaction and following reaction with an amine of the formula VII into compounds of the formula XXI

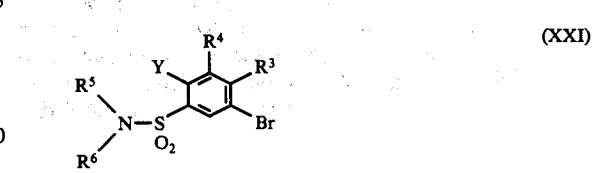

in which $R^5$ and $R^6$ are different from hydrogen.

The compounds of the formula XXI can eventually be converted by methods known from literature in an inert anhydrous solvent such as tetrahydrofurane or diethyl ether into the compounds of the formula XXII. The compounds of the formula XIII used in method (f)

are in most cases known from literature and are obtained by reaction of the thio-ureas of the formula III with α-halogenocarboxylic acids or the esters thereof of the general formula XXII

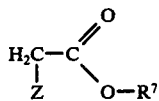 (XXII)

in which $R^7$ represents preferably hydrogen, methyl or ethyl and Z represents chlorine or bromine (R. C. Elderfield, "Heterocyclic compounds", Vol. 5, page 616, John-Wiley & Sons, Inc. 1957).

The compounds of the formula I can reacted in reversible manner in a suitable solvent with an acid of the formula H-Z. The compounds I can introduced into the pure acids at temperatures in the range of from 0° to 40° C, provided that these acids are liquid or have a melting point which is not essentially higher than 40° C and do not provoke side- reactions. It is, however, advantageous to work in a solvent, for example in water, or in an organic solvent, for example in dioxane, tetrahydrofurane, ether, an acetic acid lower alkyl ester containing 1 to 4 carbon atoms in the alkyl moiety, acetonitrile, nitromethane, acetone, methyl-ethyl ketone, etc., lower alcohols containing 1 to 4 carbon atoms having proved to be especially suitable. Per mole of the compounds I, 1 to 1.5 mole of the acids H-Z are used, it being also possible to use higher amounts of acid. It is suitable to operate at temperatures between 0° and 40° C, preferably between 10° and 25° C. The reaction is moderately exothermic.

When working in an aqueous solution, the compounds I dissolve immediately after addition of the acids H—Z and in rare cases the corresponding acid addition salts are precipitated. When a solution is obtained, the salts of the invention are isolated by mild evaporation of the water, preferably by lyophilization. When working in organic solvents, the acid addition salts often precipitate in a sparingly soluble form after addition of the respective acid H—Z. If a solution is obtained, the acid addition salts are precipitated with the aid of suitable precipitant, optionally after precious concentration. As precipitants, there are suitable the solvents described for the same purpose under method I.

The acid addition salts are often obtained in the form of viscous oils or amorphous glass-like products, even upon thorough purification. These amorphous products can be brought to crystallization in many cases optionally by heating to 40° to 80° C under treatment with an organic solvent. Solvents which promote the crystallization are in particular acetic acid lower alkyl esters having 1 to 4 carbon atoms in the alkyl moiety, for example methyl acetate, ethyl acetate, n-butyl acetate, lower dialkyl ketones such as acetone or methyl-ethyl ketone, lower dialkyl ethers such as diethyl ether, diisopropyl ether or di-n-butyl ether, as well as acetonitrile, nitromethane, and in some cases also lower alcohols such as methanol, ethanol, isopropanol or n-butanol.

The acid addition can be deprotonized to compounds of the general formula I by treatment with bases in a suitable solvent. As bases, there may be used, for example solutions of mineral hydroxides such as the hydroxides of lithium, sodium, potassium, calcium or barium, carbonates or bicarbonates such as sodium carbonate, potassium carbonate, sodium bicarbonate or potassium bicarbonate, ammonia and amines, for example triethylamine, dicyclohexylamine, piperidine, methyl-dicyclohexylamine.

When working in an aqueous medium, the free basic compounds of the formula I precipitate in a sparingly soluble form and can be separated and isolated by filtration or extraction with an organic solvent, preferably with ethyl acetate. Suitable organic reaction mediums are in particular lower alcohols containing 1 to 4 carbon atoms, preferably methanol and ethanol, but ethyl acetate, diethyl ether, tetrahydrofurane, dioxane, diethylene glycol dimethyl ether, dimethylformamide, etc. may also be used. The reaction to the compounds I takes place spontaneously. The reaction is carried out at a temperature in the range of from −35° to 100° C, preferably from 0° to 25° C. If a water-miscible organic solvent is used, the free bases of the formula I are precipitated by the addition of water, optionally after previous concentration of the reaction mixture. If a solvent which is not miscible with water is used, it is advantageous to wash the reaction mixture with water after completion of the reaction and to evaporate the organic solvent, optionally after previous drying.

Among the compounds of the invention of the formula I and their pharmacologically tolerated salts, in particular those are of interest in which $R^1$ represents methyl, ethyl, allyl or cyclopropyl, $R^2$ represents an alkyl or alkenyl radical containing 1 to 4 carbon atoms and which may be substituted by alcoxy groups of 1 to 2 carbon atoms, a cycloalkyl group containing 5 to 7 carbon atoms and benzyl, Y represents chlorine or bromine, $R^4$ represents chlorine or bromine if $R^3$ represents hydrogen or $R^3$ represents chlorine or bromine if $R^4$ represents hydrogen, and $R^5$ and $R^6$ represents hydrogen.

In addition to the 4-(3-sulfamoyl-phenyl)-1,3-thiazolidine-4-ols described in the Examples, there may also be prepared according to the invention, for example the compounds of the formula I listed in the following Tables

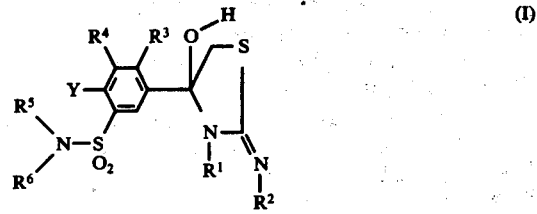 (I)

and their acid addition salts.

| No. | $R^1$ | $R^2$ | $R^3$ | $R^4$ | $R^5$ | $R^6$ | Y |
|---|---|---|---|---|---|---|---|
| 1 | $CH_3$ | $CH_2CH(CH_3)_2$ | H | Cl | H | H | Cl |
| 2 | $n$-$C_4H_9$ | $n$-$C_4H_9$ | H | Cl | H | H | Cl |
| 3 | $C_2H_5$ | —⟨H⟩ | H | Cl | H | H | Cl |

-continued

| No. | R¹ | R² | R³ | R⁴ | R⁵ | R⁶ | Y |
|---|---|---|---|---|---|---|---|
| 4 | CH₃ | cyclopentyl | H | Cl | H | H | Cl |
| 5 | cyclopropyl | cyclopropyl | H | Cl | H | H | Cl |
| 6 | CH₃ | —(CH₂)₂—C₆H₅ | H | Cl | H | H | Cl |
| 7 | C₂H₅ | —CH₂—C₆H₅ | H | Cl | H | H | Cl |
| 8 | CH₃ | CH₂CH=CH₂ | H | Cl | H | H | Cl |
| 9 | CH₂=CH—CH₂ | CH₂—CH=CH₂ | H | Cl | H | H | Cl |
| 10 | CH₃ | —(CH₂)₃—OC₂H₅ | H | Cl | H | H | Cl |
| 11 | CH₃ | —(CH₂)₄—OCH₃ | H | Cl | H | H | Cl |
| 12 | C₂H₅ | —(CH₂)₂—OC₂H₅ | H | Cl | H | H | Cl |
| 13 | CH₃ | —(CH₂)₂OC₂H₅ | H | Cl | H | H | Cl |
| 14 | CH₃ | CH₂—CH(OCH₃)—CH₃ | H | Cl | H | H | Cl |
| 15 | CH₃ | CH₃ | H | Cl | CH₃ | CH₃ | Cl |
| 16 | CH₃ | CH(CH₃)CH₂CH₃ | H | Cl | CH₃ | CH₃ | Cl |
| 17 | CH₃ | CH₂—CH(OCH₃)—CH₃ | H | Cl | H | CH₃ | Cl |
| 18 | C₂H₅ | cyclopentyl | H | Cl | H | CH₃ | Cl |
| 19 | CH₃ | —CH₂—C₆H₅ | H | Cl | H | C₂H₅ | Cl |
| 20 | CH₃ | CH₂CH=CH₂ | H | Cl | H | n-C₃H₇ | Cl |
| 21 | C₂H₅ | CH₂—CH(OCH₃)—CH₃ | H | Cl | H | n-C₄H₉ | Cl |
| 22 | CH₃ | CH₂CH(CH₃)₂ | H | Cl | H | n-C₄H₉ | Cl |
| 23 | C₂H₅ | C₂H₅ | H | Cl | H | —CH₂—C₆H₅ | Cl |
| 24 | CH₃ | cyclohexyl | H | Cl | H | —CH₂—C₆H₅ | Cl |
| 25 | C₂H₅ | C₂H₅ | H | Cl | n-C₃H₇ | n-C₃H₇ | Cl |
| 26 | C₂H₅ | C₂H₅ | H | Br | H | H | Cl |
| 27 | n-C₄H₉ | n-C₄H₉ | H | Br | H | H | Cl |
| 28 | CH₃ | CH₂—CH(CH₃)₂ | H | Br | H | H | Cl |
| 29 | CH₃ | (CH₂)₂—C₆H₅ | H | Br | H | H | Cl |
| 30 | C₂H₅ | —CH₂—C₆H₅ | H | Br | H | H | Cl |
| 31 | CH₂=CH—CH₂ | CH₂—CH=CH₂ | H | Br | H | H | Cl |
| 32 | C₂H₅ | cyclohexyl | H | Br | H | H | Cl |
| 33 | CH₃ | —CH₂—CH(OCH₃)—CH₃ | H | Br | H | H | Cl |
| 34 | CH₃ | CH₃ | H | Br | H | H | Br |
| 35 | C₂H₅ | C₂H₅ | H | Br | H | H | Br |
| 36 | C₂H₅ | CH₃CHCH₂CH₃ | H | Br | H | H | Br |
| 37 | CH₃ | cyclopentyl | H | Br | H | H | Br |
| 38 | CH₃ | —CH₂—C₆H₅ | H | Br | H | H | Br |
| 39 | CH₃ | —(CH₂)₂—OCH₃ | H | Br | H | H | Br |
| 40 | C₂H₅ | CH₂—CH(OCH₃)—CH₃ | H | Br | H | H | Br |
| 41 | CH₂=CH—CH₂ | CH₂=CH—CH₂ | H | Br | H | H | Br |
| 42 | CH(CH₃)₂ | CH(CH₃)₂ | H | Br | H | H | Br |

-continued

| No. | R¹ | R² | R³ | R⁴ | R⁵ | R⁶ | Y |
|---|---|---|---|---|---|---|---|
| 43 | $CH_3$ | $CH_3$ | H | $CH_3$ | H | H | Cl |
| 44 | $C_2H_5$ | $C_2H_5$ | H | $CH_3$ | H | H | Cl |
| 45 | n $C_4H_9$ | n $C_4H_9$ | H | $CH_3$ | H | H | Cl |
| 46 | $CH_2=CH-CH_2$ | $CH=CH-CH_2$ | H | $CH_3$ | H | H | Cl |
| 47 | $C_2H_5$ | $CH_2$-⟨phenyl⟩ | H | $CH_3$ | H | H | Cl |
| 48 | $C_2H_5$ | ⟨cyclopentyl⟩ | H | $CH_3$ | H | H | Cl |
| 49 | $CH_3$ | ⟨cyclohexyl-H⟩ | H | $CH_3$ | H | H | Cl |
| 50 | $CH_3$ | $CH_2-CH(OCH_3)-CH_3$ | H | $CH_3$ | H | H | Cl |
| 51 | $CH_3$ | $CH_3$ | H | Cl | H | H | Br |
| 52 | $C_2H_5$ | $CH_2-CH(CH_3)_2$ | H | Cl | H | H | Br |
| 53 | $CH_3$ | ⟨cyclohexyl-H⟩ | H | Cl | H | H | Br |
| 54 | $C_2H_5$ | $-(CH_2)_2$-⟨phenyl⟩ | H | Cl | H | H | Br |
| 55 | $C_2H_5$ | $CH_2-CH(OCH_3)-CH_3$ | H | Cl | H | H | Br |
| 56 | $CH_2=CH-CH_2$ | $CH_2=CH-CH_2$ | H | Cl | H | H | Br |
| 57 | $CH_3$ | $CH_3$ | H | $CH_3$ | H | H | Br |
| 58 | $C_2H_5$ | $CH(CH_3)_3$ | H | $CH_3$ | H | H | Br |
| 59 | $CH_3$ | $CH_2-CH(OCH_3)-CH_3$ | H | $CH_3$ | H | H | Br |
| 60 | $CH_3$ | ⟨cyclohexyl-H⟩ | H | $CH_3$ | H | H | Br |
| 61 | $CH_3$ | $CH_3$ | Cl | H | H | H | Br |
| 62 | $C_2H_5$ | $C_2H_5$ | Cl | H | H | H | Br |
| 63 | n-$C_4H_9$ | n-$C_4H_9$ | Cl | H | H | H | Br |
| 64 | $C_2H_5$ | $-CH(CH_3)_2$ | Cl | H | H | H | Br |
| 65 | $CH_3$ | $-CH_2-CH(OCH_3)-CH_3$ | Cl | H | H | H | Br |
| 66 | $C_2H_5$ | ⟨cyclohexyl-H⟩ | Cl | H | H | H | Br |
| 67 | $CH_3$ | $CH_2$-⟨phenyl⟩ | Br | H | H | H | Br |
| 68 | $CH_2=CH=CH_2$ | $CH_2=CH=CH_2$ | Br | H | H | H | Br |
| 69 | $C_2H_5$ | $C_2H_5$ | Br | H | H | H | Br |
| 70 | $CH_3$ | ⟨cyclopentyl⟩ | Br | H | H | H | Br |
| 71 | $CH_3$ | $CH_3$ | Br | H | H | H | Cl |
| 72 | $C_2H_5$ | $C_2H_5$ | Br | H | H | H | Cl |
| 73 | n-$C_4H_9$ | n-$C_4H_9$ | Br | H | H | H | Cl |
| 74 | $CH_3$ | $CH(CH_3)_2$ | Br | H | H | H | Cl |
| 75 | $CH_2=CH-CH_2$ | $CH_2=CH-CH_2$ | Br | H | H | H | Cl |
| 76 | $C_2H_5$ | ⟨cyclohexyl-H⟩ | Br | H | H | H | Cl |
| 77 | $CH_3$ | $-(CH_2)_2-OCH_3$ | Br | H | H | H | Cl |
| 78 | $CH_3$ | $CH_3$ | $CH_3$ | H | H | H | Cl |
| 79 | $C_2H_5$ | $C_2H_5$ | $CH_3$ | H | H | H | Cl |
| 80 | $CH_3$ | $CH_2CH(CH_3)_2$ | $CH_3$ | H | H | H | Cl |
| 81 | $CH_3$ | $CH_3$ | $CH_3$ | H | H | H | Br |
| 82 | $CH_3$ | $CH_2-CH(OCH_3)-CH_3$ | $CH_3$ | H | H | H | Br |
| 83 | $CH_2=CH-CH_2$ | $CH_2=CH-CH_2$ | $CH_3$ | H | H | H | Br |
| 84 | $CH_3$ | $CH_2$-⟨phenyl⟩ | $CH_3$ | H | H | H | Br |

The compounds of the invention are valuable medicaments and are distinguished by a very good diuretic and saluretic action.

Some patent specifications report on an anorectic, central nervous system stimulating and diuretic action of derivatives of 4-aryl-1,3-thiazolidine-4-ol (c.f. DOS 1 938 674, U.S. Pat. No. 3,671,534); these are compounds without sulfonamide groups at the aromatic nucleus and their diuretic action depends to a high degree on a specific substitution of the thiazolidine ring. It was surprising that, independently of this specific substitution at the ring, the novel compounds of the invention have a very strong salidiuretic action which is due to the introduction of a sulfonamide group into the position 3 of the benzene nucleus and which is distinctly superior qualitatively and quantitatively to that of the known thiazolidine derivatives. Moreover, the less desired anorectic and nervous system stimulating action component is largely suppressed.

The salidiuretic action of the compounds of the invention was determined on the rat with a unit dose of 50 mg/kg per os. It was found that this action was superior to the salidiuretic action of known. Commercial preparations of the thiazide group, for example the hydrochlorothiazide, and to that of chlorothalidone. In addition thereto, the novel compounds of the invention are distinguished by a long lasting action time which corresponds approximately to that of chlorothalidone. Therefore, the novel compounds of the invention are suitable in particular for the treatment of hypertonic conditions, in which case they will be combined with an antihypertonic agent as it is usual today.

Therapeutic compositions of the novel compounds are in particular tablets, dragees, capsules, suppositories as well as solutions or suspensions in ampouls for parenteral administration (i.v., s.c. and i.m.). The products of the invention are contained in these compositions preferably in the form of their acid addition salts. The therapeutical dosage unit is between 5 and 500 mg. In addition to the usual filler and carrier substances, these compositions may also contain an antihypertensive agent, especially if they are intended for the therapy of high blood pressure, for example reserpin, hydralazine, guanethidine, α-methyldopa or clonidine.

Moreover, therapeutical combination compositions with potassium-retaining compounds such as aldosterone-antagonists, for example spronolactone, or pseudo-aldosterone-antagonists such as Triamterene or Amiloride are of interest. Furthermore, the K+ - substitution may also be made with the aid of various forms for administration, for example dragees, tablets, effervescent tablets, lotions, etc.

The following Examples illustrate the invention. In these examples, the melting and decomposition points are not corrected. The infrared spectra were recorded in KBr, the indicated infrared-spectroscopic data were taken from routine spectra and have likewise not been corrected.

EXAMPLE 1

3-Ethyl-2-ethylimino-4-(3,4-dichloro-5-sulfamoylphenyl)-1,3-thiazolidine-4-ol-hydrochloride a. 3,4-Dichloro-5-sulfamoylbenzoic acid was boiled for 4 hours on a reflux condensor in 100 ml of thionyl chloride and the crystalline 3,4-dichloro-5-sulfamoylbenzoyl chloride was filtered off after standing for 20 hours at 0° C.

Colourless crystals, M.p. 195° C (decomposition).

b. 29 g of 3,4-dichloro-5-sulfamoylbenzoyl chloride while were added portionwise, while stirring, at −5° to +5° C, into an anhydrous solution of diazomethane prepared from 50 g of N-nitroso-N-methylurea in 400 ml of diethyl ether, the addition being carried out under maintenance of the safety measures necessary for the working with diazomethane, and the crystalline light yellow precipitate of 3',4'-dichloro-5'-sulfamoyldiazoacetophenone was filtered off. M.p. 206° C (decomposition).

c. 25 g of 3',4'-dichloro-5'-sulfamoyl-diazoacetophenone were introduced portionwise into a cooled and stirred mixture of 100 ml of diethyleneglycol-dimethyl ether and 50 ml of concentrated hydrochloric acid and the 2,3',4'-trichloro-5'-sulfamoylaceto-phenone was precipitated with 1 liter of water.

Colourless crystals, M.p. 191° C (from isopropanol).

d. 6 g of 2,3',4'-trichloro-5'-sulfamoyl-acetophenone and 2,6 g of 1,3-diethyl-thiourea were heated for 15 minutes to 40° C in 40 ml of methanol, the 3-ethyl-2-ethylimino-4-ol-hydrochloride was precipitated with 200 ml of diisopropyl ether and crystallized from ethyl acetate.

Colourless crystals. M.p. 158° C.

EXAMPLE 2

3-(3,4-Dichloro-5-sulfamoylphenyl)-3-hydroxy-2,3,6,7-tetrahydro-5H-thiazolo[3,2-a]-pyrimidine-hydrochloride was obtained in a manner analogous to the method described in Example 1 d from 2,3',4'-trichloro-5'-sulfamoyl-acetophenone and 2,35 g of 3,4,5,6-tetrahydro-2-pyrimidine-thiol. M.p. 188° C (decomposition).

EXAMPLE 3

4-(3,4-Dichloro-5-sulfamoylphenyl)-3-isopropyl-2-isopropylimino-1,3-thiazolidine-4-ol-hydrochloride was obtained in a manner analogous to the method described in Example 1 d from 6.1 g of 2,3',4'-trichloro-5'-sulfamoylacetophenone and 1,3-diisopropyl-thiourea. M.p. 171° C (decomposition).

EXAMPLE 4

4-(2,4-Dichloro-5-sulfamoylphenyl)-3-methyl-2-methylimino-1,3-thiazolidine-4-ol-hydrobromide a. 8 g of 2',4'-dichloro-5'-nitro-acetophenone were boiled for 4 hours under reflux in 31 ml of ethanol, after addition of 6.1 g of iron turnings and 6.5 ml of concentrated hydrochloric acid. After evaporation of the solvent, the mixture was combined with water, extracted with ethyl acetate and the 5'-amino-2',4'-dichloroacetophenone was isolated by concentration of the ethyl acetate.

Colourless crystals, M.p. 74° C.

b. 33 g of 5'-amino-2',4'-dichloroacetophenone were suspended in 330 ml of hydrochloric acid of 18% strength and diazotized at 0° C with a solution of 11.6 g of sodium nitrite in 30 ml of water. The cold solution of the diazonium chloride was then added portionwise to a stirred suspension of 400 ml of a solution of glacial acetic acid saturated with $SO_2$ and 13 g of copper-II-chloride-dihydrate, the whole was stirred for 15 minutes at room temperature and the 2',4'-dichloro-5'-chlorosulfonyl-acetophenone was precipitated with 800 ml of water. M.p. 71° C.

c. 4.7 g of 2',4'-dichloro-5'-chlorosulfonyl-acetophenone were introduced into a mixture of 20 ml of aqueous ammonia (25%) and 20 ml of methanol. After having allowed to whole to stand for 10 hours, one half of the reaction volume was evaporated and the crystalline 2',4'-dichloro-5'-sulfamoyl-acetophenone was filtered off. M.p. 166° C.

d. 20 ml of a solution of 16 g bromine in 60 ml of ethyl acetate was run into a suspension of 26.8 g of 2',4'-dichloro-5'-sulfamoyl-acetophenone in 250 ml of ethyl acetate and the whole was boiled under reflux until the bromine colour disappeared suddenly. The mixture was allowed to cool, the remaining bromine solution was added dropwise at 20° to 30° C, the solvent was removed and, after addition of a small amount of ethyl acetate, the crystalline 2-bromo-2',4'-dichloro-5'-sulfamoyl-acetphenone was filtered off with suction. M.p. 119°–121° C.

e. 7 g of 2-bromo-2',4'-dichloro-5'-sulfamoylacetophenone and 2.5 g of 1,3-dimethyl-thiourea were allowed to react for 20 hours in 50 ml of methanol, the precipitate of 4-(2,4-dichloro-5-sulfamoylphenyl)-3-methyl-2-methylimino-1,3-thiazolidine-4-ol-hydrobromide was filtered off and washed with acetone.

M.p. 239° C (decomposition).

EXAMPLE 5

3-(2,4-Dichloro-5-sulfamoylphenyl)-3-hydroxy-2,3,5,6-tetrahydroimidazo[2,1-b]-thiazole-hydrobromide was obtained in a manner analogous to the method described in Example 4 e from 3.5 g of 2-bromo-2',4'-dichloro-5'-sulfamoylacetophenone and 1 g of imidazolidine-2-thione. Mp. 225° C (decomposition).

EXAMPLE 6

3-Ethyl-4-(2,4-dichloro-5-sulfamoylphenyl)-2-isobutylimino-1,3-thiazolidine-4-ol-hydrobromide was obtained by the reaction of 2.5 g of 2-bromo-2',4'-dichloro-5'-sulfamoyl-acetophenone with 1.6 g of 1-ethyl-3-isobutyl-thiourea in 30 ml of acetone for 24 hours at room temperature and subsequent precipitation with 30 ml of ethyl acetate. M.p. 208° C (decomposition).

EXAMPLE 7

4-(2,4-Dichloro-5-sulfamoylphenyl)-2-cyclohexylimino-3-methyl-1,3-thiazolidine-4-ol-hydrobromide was obtained in a manner analogous to Example 6 from 3.5 g of 2-bromo-2',4'-dichloro-5'-sulfamoyl-acetophenone and 1.7 g of 1-cyclohexyl-3-methylthiourea. M.p. 132° C (decomposition).

EXAMPLE 8

3-Allyl-2-allylimino-4-(2,4-dichloro-5-sulfamoylphenyl)-1,3-thiazolidine-4-ol-hydrobromide was obtained in a manner analogous to Example 6 from 3,5 g of 2-bromo-2',4'-dichloro-5'-sulfamoyl-acetophenone and 1,3-diallyl-thio-urea. M.p. 202° C (decomposition).

EXAMPLE 9

3-Ethyl-2-ethylimino-4-(2,4-dichloro-5-sulfamoylphenyl)-1,3-thiazolidine-4-ol-hydrobromide was obtained in a manner analogous to that described in Example 1 d) from 3.5 g of 2-bromo-2',4'-dichloro-5'-sulfamoyl-acetophenone and 1.3 g of 1,3-diethyl-thiourea. M.p. 202° C (decomposition).

EXAMPLE 10

4-(2,4-Dichloro-5-sulfamoylphenyl)-3-cyclohexyl-2-cyclohexylimino-1,3-thiazolidine-4-ol-hydrobromide 2.4 g of 1,3-dicyclohexyl-thiourea were added to 3,5 g of 2-bromo-2',4'-dichloro-5'-sulfamoylacetophenone in 40 ml of ethyl acetate. The whole was allowed to stand overnight at 20° C, the crystals were filtered off and washed with ethyl acetate. M.p. 161°-163° C.

EXAMPLE 11

4-(2,4-Dichloro-5-sulfamoylphenyl)-3-cyclopropyl-2-cyclopropylimino-1,3-thiazolidine-4-ol-hydrobromide was obtained in a manner analogous to that described in Example 10 from 3.5 g of 2-bromo-2',4'-dichloro-5'-sulfamoylacetophenone and 1.6 g of 1,3-dicyclopropyl-thiourea. M.p. 226° C (decomposition).

EXAMPLE 12

3-Butyl-2-butylimino-4-(2,4-dichloro-5-sulfamoylphenyl)-1,3-thiazolidine-4-ol-hydrobromide was obtained in a manner analogous to the method described in Example 10 from 3.5 g of 2-bromo-2',4'-dichloro-5'-sulfamoylacetophenone and 1.9 g of 1.3-dibutyl-thiourea. M.p. 194° C (decomposition).

EXAMPLE 13

2-Benzylimino-4-(2,4-dichloro-5-sulfamoylphenyl)-3-methyl-1,3-thiazolidine-4-ol-hydrobromide was obtained in a manner analogous to the method described in Example 10 from 3.5 g of 2-bromo-2',4'-dichloro-5'-sulfamoylacetophenone and 1.8 g of 1-benzyl-3-methyl-thiourea. Mp. 173° C (decomposition).

EXAMPLE 14

4-(2,4-Dichloro-5-sulfamoylphenyl)-3-methyl-2-(2-phenylethylimino)-1,3-thiazolidine-4-ol-hydrobromide was obtained in a manner analogous to the method described in Example 10 from 3.5 g of 2-bromo-2',4'-dichloro-5'-sulfamoylacetophenone and 2 g of 1-methyl-3-(2-phenylethyl)-thiourea. M.p. 164°-165° C (decomposition)

EXAMPLE 15

4-(2,4-dichloro-5-sulfamoylphenyl)-3-methyl-2-(2-methoxypropylimino)-1,3-thiazolidine-4-ol-hydrobromide was obtained in a manner analogous to the method described in Example 10 from 3.5 g of 2-bromo-2',4'-dichloro-5'-sulfamoylacetophenone and 1.6 g of 1-methyl-3-(2-methoxypropyl)-thiourea. M.p. 196° C (decomposition).

EXAMPLE 16

4-(2,4-Dichloro-5-sulfamoylphenyl)-3-methyl-2-methylimino-1,3-thiazolidine-4-ol 7.4 g of 4-(2,4-dichloro-5-sulfamoylphenyl)-3-methyl-2-methylimino-1,3-thiazolidine-4-ol-hydrobromide in 60 ml of methanol were combined with 4 ml of triethylamine, heated for 5 minutes to 50° C on the steam bath and precipitation was effected with 250 ml of water. M.p. 187°-190° C (decomposition).

EXAMPLE 17

4-(3,4-Dimethyl-5-sulfamoylphenyl)-3-methyl-2-methylimino-1,3-thiazolidine-4-ol-hydrobromide a. 54.g of 3,4-dimethyl-5-sulfamoyl-benzoic acid were boiled in 600 ml of thionyl chloride until the development of HCl ceased, the excess of thionyl chloride was evaporated under reduced pressure and the remaining 3,4-dimethyl-5-sulfamoyl-benzoyl chloride was filtered off after the addition of 150 ml of diisopropyl ether. M.p. 168° C.

b. 25 g of 3,4-dimethyl-5-sulfamoyl-benzoyl chloride were introduced in a manner analogous to that described in Example 1 b into an anhydrous solution of diazomethane, prepared from 40 g of N-nitroso-N-methylurea, in 800 ml of diethyl ether, whereupon the 3',4'-dimethyl-5'-sulfamoyl-diazoacetophenone was obtained. M.p. 174° C (decomposition).

c. 12.7 g of 3',4'-dimethyl-5'-sulfamoyl-diazoacetophenone were reacted in a manner analogous to that described in Example 1 c with a mixture of 20 ml of 48% hydrobromic acid in 100 ml of diethyleneglycol-dimethyl ether and the 2-bromo-3',4'-dimethyl-5'-sulfamoyl-acetophenone was then worked up. M.p. 169° C.

d. 3.1 g of 2-bromo-3',4'-dimethyl-5'-sulfamoyl-acetophenon were reacted according to the method described in Example 6 with 1.1 g of 1,3-dimethyl-thiourea and the 4-(3,4-dimethyl-5-sulfamoylphenyl)-3-methyl-2-methylimino-1,3-thiazolidine-4-ol-hydrobromide was filtered off. M.p. 252°–255° C (decomposition).

EXAMPLE 18

3-Ethyl-4-(3,4-dimethyl-5-sulfamoylphenyl)-2-isobutylimino-1,3-thiazolidine-4-ol-hydrobromide was obtained in a manner analogous to the method described in Example 6 from 3.1 g of 2-bromo-3',4'-dimethyl-5'-sulfamoylacetophenone and 1.7 g of 1-ethyl-3-isobutyl-thiourea. M.p. 145° C (decomposition).

EXAMPLE 19

3-Allyl-2-allylimino-(3,4-dimethyl-5-sulfamoylphenyl)-1,3-thiazolidine-4-ol-hydrobromide was obtained in a manner analogous to the method described in Example 6 in amorphous form from 3.1 g of 2-bromo-3',4'-dimethyl-5'-sulfamoyl-acetophenone and 1.6 g of 1,3-diallyl-thiourea and the substance was brought to crystallization under ether. M.p. 138°–140° C (decomposition).

EXAMPLE 20

4-(3,4-Dimethyl-5-sulfamoylphenyl)-3-methyl-2-methylimino-1,3-thiazolidine-4-ol was obtained from 2.5 g of 4-(3,4-dimethyl-5-sulfamoylphenyl)-3-methyl-2-methylimino-1,3-thiazolidine-4-ol-hydrobromide in 150 ml of 40° hot water with 10 ml of 2N-ammonia and a 2 hours stirring at room temperature. M.p. 187° C (decomposition).

EXAMPLE 21

4-(3-Bromo-4-chloro-5-sulfamoylphenyl)-3-methyl-2-methylimino-1,3-thiazolidine-4-ol-hydrobromide a. 8.8 g of 3-bromo-4-chloro-5-sulfamoyl-benzoic acid (m.p. 270° C) in 100 ml of thionyl chloride were converted in a manner analogous to the method described in Example 17 a) into the 3-bromo-4-chloro-5-sulfamoylbenzoyl chloride (M.p. 200° C).

b. 33 g of 3-bromo-4-chloro-5-sulfamoyl-benzoyl chloride were reacted in a manner analogous to the method described in Example 1 b) with diazomethane to yield the 3'-bromo-4'-chloro-5'-sulfamoyl-diazoacetophenone and worked up. M.p. 193° C (decomposition).

c. From 6 g of 3'-bromo-4'-chloro-5'-sulfamoyl-acetophenone, there was obtained according to the method described in Example 17 c the 2,3'-dibromo-4'-chloro-5'-sulfamoyl-acetophenone (M.p. 185° C) which was converted according to the method described in Example 1 d with 2.4 g of 1,3-dimethyl-thiourea into the 4-(3-bromo-4-chloro-5-sulfamoylphenyl)-3-methyl-2-methylimino-1,3-thiazolidine-4-ol-hydrobromide. M.p. 202° C (decomposition).

EXAMPLES 22

4-(3-Chloro-4-methyl-5-sulfamoylphenyl)-3-methyl-2-methylimino-1,3-thiazolidine-4-ol-hydrobromide a. 7 g of 3-chloro-4-methyl-5-sulfamoyl-benzoic acid (M.p. 252° C) were reacted with 70 ml of thionyl chloride in a manner analogous to that described in Example 17 a) into the 3-chloro-4-methyl-5-sulfamoyl-benzoyl chloride. M.p. 168° C.

b. 26.7 g of 3-chloro-4-methyl-5-sulfamoyl-benzoyl chloride were reacted in a manner analogous to that described in Example 1 b with diazomethane to yield the 3'-chloro-4'-methyl-5'-sulfamoyl-diazoacetophenone, M.p. 184° C.

c. From 7 g of 3'-chloro-4'-methyl-5'-sulfamoyl-diazoacetophenone, there was obtained according to the method described in Example 17 c) the 2-bromo-3'-chloro-4'-methyl-5'-sulfamoylacetophenone. M.p. 174°–176° C.

d. 3.2 g of 2-bromo-3'-chloro-4'-methyl-5'-sulfamoyl-acetophenone were reacted according to the method described in Example 6 with 1.2 g of 1,3-dimethyl-thiourea to yield the 4-(3-chloro-4-methyl-5-sulfamoyl-pheny)-3-methyl-2-methylimino-1,3-thiazolidine-4-ol-hyrobromide. M.p. 160° C (decomposition).

EXAMPLE 23

3-(2,4-Dichloro-5-sulfamoylphenyl)-3-hydroxy-2,3,5,6-tetrahydro-imidazo[2,1-b]-thiazole-hydrobromide a. 2 g of thioacetic acid were dissolved under an atmosphere of an inert gas (nitrogen) in 20 ml of ethanol and neutralized exactly with a 40% aqueous potassium hydroxide solution. Then, 7 g of 2-bromo-2'-4'-dichlor-5'-sulfamoylacetophenone were added and the whole was stirred for 3 hours at 20° C. The reaction mixture was poured into 100 ml of water, while stirring, the solid precipitate of 2-acetylthio-2',4'-dichloro-5'-sulfamoylacetophenone was filtered off, introduced without purification into 70 ml of a 5% aqueous sodium hydroxide solution under nitrogen, stirred for 90 minutes at 20° C and adjusted to pH 1 with the aid of 2N-hydrochloric acid. The crystalline 2',4'-dichloro-5'-sulfamoyl-acetophenone-2-thiole was filtered off and washed several times with water. Light yellow crystals; M.p. 78°–81° C.

b. 6 g of 2',4'-dichloro-5'-sulfamoyl-acetophenone-2-thiole were added portionwise, at −10° C, under an atmosphere of nitrogen, to 3 g of 2-bromo-1-imidazoline in 50 ml of isopropanol, the whole was stirred for 10 ahours at 20° C and for 1 hour at 35° C and the 3-(2,4-dichloro-5-sulfamoylphenyl)-3-hydroxy-2,3,5,6-tetrahydroimidazo[2,1-b]thiazole-hydrobromide was precipitated with 100 ml of diethyl ether. The viscous amorphous product was brought to crystallization under methanol and under acetone. M.p. 215°–221° C (decomposition).

EXAMPLE 24

4-(3,4-Dichloro-5-sulfamoylphenyl)-3-methyl-2-methylimino-1,3-thiazolidine-4-ol-hydrobromide a. 25 g of 3',4'-dichloro-5'-sulfamoyl-diazoacetophenone were converted in a manner analogous to the method described in Example 1 c) with 50 ml of 48% hydrobromic acid into the 2-bromo-3',4'-dichloro-5'-sulfamoyl-acetophenone. M.p. 180° C.

b. From 3.5 g of 2-bromo-3',4'-dichloro-5'-sulfamoyl-acetophenone and 1,2 g of 1,3-dimethyl-thiourea, there was obtained the 4-(3,4-dichloro-5-sulfamoylphenyl)-3-methyl-2-methylimino-1,3-thiazolidine-4-ol-hydrobromide. M.p. 169°–170° C (decomposition).

EXAMPLE 25

4-(2,4-Dichloro-5-sulfamoylphenyl)-3-methyl-2-methylimino-1,3-thiazolidine-4-ol a. 20 g of 2,4-dichloro-5-chlorosulfonyl-acetphenone were reacted in a manner analogous to the method described in Example 4 d with 11.2 g of bromine in 200 ml of ethyl acetate, the solvent was removed and the remaining 2-bromo-2',4'-dichloro-5'-chlorosulfonyl-acetophenone was crystallized under diisopropyl ether. M.p. 84°–85° C. 5.5 g of 1,3-dimethyl-thiourea were added to 18.8 g of 2-bromo-2',4'-dichloro-5'-chlorosulfonyl-acetophenone in 150 ml of ethyl acetate, the whole was stirred for 3 hours at room temperature and the crystalline 4-(2,4-dichloro-5-chlorosulfonylphenyl)-3-methyl-2-methylimino-1,3-thiazolidine-4-ol-hydrobromide was filtered off. M.p. 202° C (decomposition).

c. 4.4 g of 4-(2,4-dichlor-5-chlorosulfonylphenyl)-3-methyl-2-methylimino-1,3-thiazolidine-4-ol-hydrobromide were introduced, while stirring, into a solution of 10 g of gaseous ammonia in 70 ml of methanol. After having allowed the whole to stand overnight at room temperature, the solution was concentrated to about 30 ml of its volume under reduced pressure and the 4-(2,4-dichloro-5-sulfamoylphenyl)-3-methyl-2-methylimino-1,3-thiazolidine-4-ol was precipitated with 100 ml of water. M.p. 186°–189° C (decomposition ).

EXAMPLE 26

By the reaction of 4.4 g of 4-(2,4-dichloro-5-chlorosulfonylphenyl)-3-methyl-2-methylimino-1,3-thiazolidine-4-ol-hydrobromide, there was obtained according to the method described in Example 25 c a. with 4 g of a 40% methylamine solution, the 4-(2,4-dichloro-5-methylsulfamoylphenyl)-3-methyl-2-methylimino-1,3-thiazolidine-4-ol, M.p. 188° C (decomposition);

b. with 2.5 g of n-propylamine, the 4-(2,4-dichloro-5-propylsulfamoyl-phenyl)-3-methyl-2-methylimino-1,3-thiazolidine-4-ol, M.p. 180° C (decomposition);

c. with 1.8 g of β-phenylethylamine and 4 g of triethylamine, the 4-[2,4-dichloro-5-(2-phenyl-ethylsulfamoyl)-phenyl]-3-methyl-2-methylimino-1,3-thiazolidine-4-ol, M.P. 163° C (decomposition);

d. with 4 g of di-n-propylamine, the 4-(2,4-dichloro-5-di-n-propylsulfamoyl-phenyl)-3-methyl-2-methylimino-1,3-thiazolidine-4-ol. M.p. 165° C (decomposition).

EXAMPLE 27

4-(5-N-Benzyl-N-methylsulfamoyl-2,4-dichloro-phenyl)-3-methyl-2-methylimino-1,3-thiazolidine-4-ol-hydrobromide 3.6 g of 2-bromo-5'-N-benzyl-N-methylsulfamoyl-2',4'-dichloroacetophenone were reacted in a manner analogous to the method described in Example 10 with 0.8 g of 1,3-dimethylthiourea and the amorphous precipitate was brought to crystallization by gentle heating. M.p. 156° C (decomposition).

EXAMPLE 28

4-(5-sec.Butylsulfamoyl-2,4-dichloro-phenyl)-3-methyl-2-methyl-imino-1,3-thiazolidine-4-ol-hydrobromide 2.3 g of 2-bromo-5'-sec. butylsulfamoyl-2',4'-dichloro-acetophenone were reacted in a manner analogous to the method described in Example 10 with 0.6 g of 1,3-dimethyl-thiourea and brought to crystallization in a manner analogous to that described in Example 27. M.p. 173° C (decomposition).

EXAMPLE 29

4-(2,4-Dichloro-5-dimethylsulfamoyl-phenyl)-3-methyl-2-methylimino-1,3-thiazolidine-4-ol-hydrobromide 1.9 g of 2-bromo-2',4'-dichloro-5'-dimethylsulfamoyl-aceto were reacted in a manner analogous to the method described in Example 10 with 0.5 g of 1,3-dimethyl-thiourea, M.p. 202° C (decomposition).

EXAMPLE 30

4-(2,4-Dichloro-5-dimethylsulfamoyl-phenyl)-3-cyclohexyl-2-cyclohexylimino-1,3-thiazolidine-4-ol-hydrobromide 3.1 g of 2-bromo-2',4'-dichloro-5'-dimethylsulfamoyl-acetophenone were reacted in a manner analogous to the method described in Example 10 with 1,3-dicyclohexyl-thiourea. M.P. 182° C (decomposition).

EXAMPLE 31

4-(5-Benzylsulfamoyl-2,4-dichloro-phenyl)-3-methyl-2-methylimino-1,3-thiazolidine-4-ol-hydrobromide 2,2 g of 5'-benzylsulfamoyl-2-bromo-2',4'dichloroacetophenone were reacted in a manner analogous to the method described in Example 10 with 0.5 g of 1,3-dimethyl-thiourea. M.p. 201° C (decomposition).

EXAMPLE 32

Preparation of the pre-stages required in the Examples 27 through 31

A. 4.3 g of 2',4'-dichloro-5'-chlorosulfonyl-acetophenone in 15 ml of methanol a. were allowed to stand overnight at 20° C with 1 g of benzylamine, poured into 200 ml of water, adjusted to pH 1-3 by means of hydrochloric acid and the crystalline 5'-benzylsulfamoyl-2',4'-dichloro-acetophenone was filtered off. Mp. 116°–117° C.

b. were reacted with 6 g of a 40% aqueous dimethylamine solution in a manner analogous to that described in this Example under A a and the 2',4'-dichloro-5'-dimethylsulfamoyl-acetophenone was isolated. M.p. 98°–100° C (from diisopropyl ether).

c. were reacted with 1 g of N-benzyl-N-methylamine and 1.5 g of triethylamine in a manner analogous to the method described in this Example under A a) to yield the 5'-N-benzyl-N-methylsulfamoyl-2',4'-dichloro-acetophenone. M.p. 109° C.

d. were reacted with 3 g of sec. butylamine in a manner analogous to the method described in this Example under A a) to yield the 5'-sec. butylsulfamoyl-2',4'-dichloro-acetophenone. M.p. 109° C.

B. In a manner analogous to the method described in Example 4 d), there was obtained a. from 5.3 g of 2',4'-dichloro-5'-dimethylsulfamoyl-acetophenone and 2.3 g of bromine in 20 ml of ethyl acetate, the 2-bromo-2',4'-dichloro-5'-dimethylsulfamoyl-acetophenone. M.p. 133° C.

b. from 5.2 g of 5'-benzylsulfamoyl-2',4'-dichloro-acetophenone and 2.3 g of bromine in 20 ml of ethyl acetate, the 5'-benzylsulfamoyl-2-bromo-2',4'-dichloro-acetophenone. M.p. 103° C.

c. from 2.7 g of 5'-N-benzyl-N-methylsulfamoyl-2',4'-dichloro-acetophenone and 1.1 g of bromine in 15 ml of ethyl acetate, the 5'-N-benzyl-N-methylsulfamoyl-2-bromo-2',4'-dichloro-acetophenone (in the form of an oil).

d. 1.7 g of 5'-sec.butylsulfamoyl-2',4'-dichloro-acetophenone and 0.8 g of bromine in 10 ml of ethyl acetate, the 2-bromo-5'-sec.butyl-2',4'-dichloro-acetophenone (in the form of an oil).

We claim:
1. Thiazolidine derivatives of the general formula I

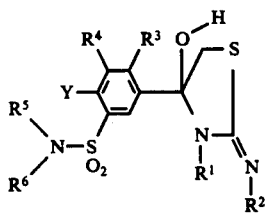

in which $R^1$ represents alkyl or alkenyl radicals of 1 to 4 carbon atoms, cycloalkyl groups of 3 to 6 carbon atoms, $R^2$ represents an alkyl or alkenyl group of 1 to 6 carbon atoms which may be substituted by alkoxy groups of 1 to 2 carbon atoms, cycloalkyl groups of 3 to 8 carbon atoms, phenylalkyl groups of 1 to 2 carbon atoms in the alkyl moiety, and in which $R^1$ and $R^2$ together may represent an alkylene chain of 2 to 4 carbon atoms which may be branched, Y represents chlorine, bromine or methyl and $R^3$ and $R^4$ represent hydrogen, chlorine, bromine or methyl, the two radicals $R^3$ and $R^4$ representing at the same time neither hydrogen, nor chlorine, bromine or methyl, $R^5$ and $R^6$ represent hydrogen or lower alkyl of 1 to 4 carbon atoms, $R^6$ may additionally represent a phenylalkyl group, and their acid addition salts with physiologically tolerated acids.

2. A compound as claimed in claim 1, which is 4-(3,4-dichloro-5-sulfamoylphenyl)-3-methyl-2-methyl-imino-1,3-thiazolidine-4-ol-hydrobromide.

3. A compound as claimed in claim 1, which is 3-ethyl-2-ethylimino-4-(3,4-dichloro-5-sulfamoyl-phenyl)-1,3-thiazolidine-4-ol-hydrochloride.

4. A compound as claimed in claim 1, which is 4-(3,4-dichloro-5-sulfamoylphenyl)-3-isopropyl-2-isopropyl-imino-1,3-thiazolidine-4-ol-hydrochloride.

5. A compound as claimed in claim 1, which is 4-(2,4-dichloro-5-sulfamoylphenyl)-3-methyl-2-methylimino-1,3-thiozolidine-4-ol.

6. A compound as claimed in claim 1, which is 3-ethyl-2-ethyleimino-4-(2,4-dichloro-5-sulfamoyl-phenyl)-1,3-thiazolidine 4-ol-hydrobromide.

7. A compound as claimed in claim 1, which is 3-(2,4-dichloro-5-sulfamoylphenyl)-3-hydroxy-2,3,5,6-tetrahydroimidazo[2,1- b]thiazole-hydrobromide.

* * * * *